(12) United States Patent
Chang et al.

(10) Patent No.: US 11,752,285 B2
(45) Date of Patent: Sep. 12, 2023

(54) SYSTEM AND METHOD FOR ACCURATE ESTIMATION OF INTENTIONAL AND UNINTENTIONAL LEAKS IN FLOW GENERATION SYSTEMS

(71) Applicant: INVENT MEDICAL CORPORATION, Carlsbad, CA (US)

(72) Inventors: Samuel M. Chang, Poway, CA (US); Nhien M. Nguyen, Santa Ana, CA (US)

(73) Assignee: INVENT MEDICAL CORPORATION, Carlsbad, CA (US)

( * ) Notice: Subject to any disclaimer, the term of this patent is extended or adjusted under 35 U.S.C. 154(b) by 294 days.

(21) Appl. No.: 16/950,832

(22) Filed: Nov. 17, 2020

(65) Prior Publication Data

US 2021/0060273 A1    Mar. 4, 2021

Related U.S. Application Data

(62) Division of application No. 15/498,601, filed on Apr. 27, 2017, now Pat. No. 10,869,977.

(Continued)

(51) Int. Cl.
*A61M 16/00* (2006.01)
*A61M 16/10* (2006.01)
(Continued)

(52) U.S. Cl.
CPC .... *A61M 16/0069* (2014.02); *A61M 16/0051* (2013.01); *A61M 16/026* (2017.08);
(Continued)

(58) Field of Classification Search
CPC .............. A61M 16/00; A61M 16/0051; A61M 16/0057; A61M 16/0063; A61M 16/0066; A61M 16/0069; A61M 16/022; A61M 16/024; A61M 16/026; A61M 16/06; A61M 16/0666; A61M 16/08; A61M 16/0875;
(Continued)

(56) References Cited

U.S. PATENT DOCUMENTS

| 3,025,052 | A1 | 9/2011 | Matthews et al. |
| 2002/0023645 | A1* | 2/2002 | Zdrojkowski ....... A61M 16/026 |
| | | | 128/204.23 |

(Continued)

*Primary Examiner* — Joseph D. Boecker
(74) *Attorney, Agent, or Firm* — Procopio, Cory, Hargreaves & Savitch LLPP

(57) ABSTRACT

In one embodiment, a method for accurate leak estimation in a flow generation system includes measuring a total flow through the flow generation system, measuring a pressure in in the primary flow circuit of the flow generation system, determining when the measured pressure is within a predetermined threshold of EPAP, and calculating an intentional leak flowrate and an unintentional leak flowrate based on the relationship $Q_{FS}(t)=Q_{IL}(t)+Q_{UL}(t)$ when the measured pressure is within the predetermined threshold. In another embodiment, a flow generation system includes in one embodiment an airflow generator connected in-line to a flow sensor, a pressure sensor and a patient interface connection by a first gas flow circuit, and a controller electrically coupled to the airflow generator, the flow sensor and the pressure sensor.

20 Claims, 17 Drawing Sheets

Related U.S. Application Data

(60) Provisional application No. 62/328,675, filed on Apr. 28, 2016.

(51) Int. Cl.

| | | |
|---|---|---|
| *G01M 3/28* | (2006.01) | |
| *A61M 16/12* | (2006.01) | |
| *A61M 16/16* | (2006.01) | |
| *A61M 16/20* | (2006.01) | |
| *G01M 3/26* | (2006.01) | |
| *A61M 16/06* | (2006.01) | |

(52) U.S. Cl.
CPC .... *A61M 16/1005* (2014.02); *A61M 16/1045* (2013.01); *A61M 16/1055* (2013.01); *A61M 16/125* (2014.02); *A61M 16/16* (2013.01); *A61M 16/208* (2013.01); *G01M 3/26* (2013.01); *G01M 3/28* (2013.01); *A61M 16/0672* (2014.02); *A61M 2016/0027* (2013.01); *A61M 2016/0033* (2013.01); *A61M 2016/0039* (2013.01); *A61M 2202/0208* (2013.01); *A61M 2205/15* (2013.01); *A61M 2205/50* (2013.01); *A61M 2230/40* (2013.01)

(58) Field of Classification Search
CPC .......... A61M 16/0883; A61M 16/0891; A61M 16/10; A61M 16/1005; A61M 16/1045; A61M 16/1055; A61M 16/1075; A61M 16/109; A61M 16/12; A61M 16/125; A61M 16/16; A61M 16/208; A61M 2016/0027; A61M 2016/0039; A61M 2205/15; A61M 2205/50

See application file for complete search history.

(56) References Cited

U.S. PATENT DOCUMENTS

| | | | |
|---|---|---|---|
| 2002/0088465 A1 | 7/2002 | Hill | |
| 2009/0241951 A1* | 10/2009 | Jafari | A61M 16/06 128/204.21 |
| 2011/0196251 A1 | 8/2011 | Jourdain et al. | |
| 2011/0259330 A1* | 10/2011 | Jafari | A61M 16/024 702/51 |
| 2012/0060841 A1 | 3/2012 | Crawford, Jr. et al. | |
| 2013/0110416 A1* | 5/2013 | Hill | G06F 17/18 702/46 |
| 2013/0118496 A1 | 5/2013 | Truschel et al. | |
| 2013/0267863 A1 | 10/2013 | Orr | |
| 2014/0109907 A1 | 4/2014 | Doshi et al. | |
| 2014/0194767 A1* | 7/2014 | Zheng | A61B 5/087 600/538 |
| 2015/0107584 A1 | 4/2015 | Jafari et al. | |
| 2016/0022954 A1* | 1/2016 | Bath | A61M 16/16 128/203.12 |
| 2016/0151590 A1 | 6/2016 | Porcyk | |
| 2017/0319812 A1 | 11/2017 | Truschel et al. | |
| 2018/0200464 A1* | 7/2018 | Borrello | A61M 16/026 |
| 2018/0256841 A1* | 9/2018 | Borrello | A61M 16/024 |

* cited by examiner

SYSTEM AND METHOD FOR ACCURATE ESTIMATION OF INTENTIONAL AND UNINTENTIONAL LEAKS IN FLOW GENERATION SYSTEMS

CROSS-REFERENCE TO RELATED APPLICATIONS

This application is a divisional of U.S. application Ser. No. 15/498,601, filed on Apr. 27, 2017, which claims priority to U.S. provisional application No. 62/328,675 filed on Apr. 28, 2016 incorporated herein by reference in its entirety.

BACKGROUND OF THE INVENTION

Flow generation systems can be generally described as systems that generate a gaseous flow, for example airflow or a blend of ambient air and oxygen. A ventilator is one example of a flow generation system. A ventilator is a piece of medical equipment that delivers a flow of gas, such as a blend of oxygen and ambient air to the airway of a patient to assist in or substitute a patient's breathing. Many ventilators deliver a blend of oxygen and air so that the patient receives a target oxygen concentration greater than that of ambient air. Generally, ventilators utilize a combination of single-use or reusable disposable components for the patient interface (e.g. a mask or mouthpiece connected to flexible tubing) and non-disposable capital equipment (e.g. air pumps, sensors, controller modules, humidifiers, etc.) that is used over a period of time among different patients. The patient interface can be for example a mouthpiece, mask (full face, nasal, pillow, total mask, or combinations of these), nasal cannula, endotracheal tube or tracheostomy tube.

When any patient interface such as patient tubing, masks, mouth piece, etc. is used on a flow generation system such as a ventilator, leak is inherent to the system. For "blower-based" systems, intentional leak is created to prevent $CO_2$ rebreathing. However, there will be unintentional leaks as well, typically from masks that are not well fitted, dislodging of masks due to patient's movement, or other causes. Conventional systems typically apply large time constant filtering techniques to smooth out the total flow in an attempt to estimate the leaks in the patient system. These techniques yield a single leak estimate throughout each patient breaths, or at most, a finite number of leak estimate values with respect to the breathing cycles.

The majority of ventilator and patient data as well as ventilator performance depend on accurate leak estimates. Ventilator functions that could change based on calculated leak estimates include tidal volume, minute volume, breath trigger and breath cycle. Various techniques have been proposed for calculating leak estimates. For example, expiratory flow adjustment techniques can be used. Some ventilator systems ask the user to enter specific mask types or patient interfaces in use. For unintentional leaks, the ventilator calculates a baseline flow at the end of each breath exhalation. Since patient flow can assumed be to be zero at the end of exhalation, any difference between actual patient flow and original baseline flow may represent unintentional leak. Tidal volume adjustment techniques can also be used. This adjustment is based on the comparison between inspiratory and expiratory tidal volumes. Any difference between the two is assumed to be an unintentional circuit leak. Both of the techniques described above are used to find a baseline leak flow that can be compared to measured flow. Leak tolerance can also be quantified using various techniques, including averaging (e.g. average volume), parabolic leak (e.g. proportional to the square of the patient pressure), and patient flow (e.g. total circuit flow: leak plus patient flow). These methods also rely on baseline calculations and several breaths of leak measure averaging. When the leak estimate is not accurate, ventilators cannot function satisfactorily. This inaccuracy can get much worse when there are unintentional leaks in the patient system.

Without accurate leak estimates, vital patient and ventilator data will not be accurate. Many times, clinicians make ventilator settings adjustments based on the patient and ventilator data which relies on accurate leak estimates. When the patient and ventilator data is not accurate, patients will not be able to get optimum treatments. Some examples of these patient and ventilator data which are affected by leak estimate include inspired and exhaled tidal volume, minute ventilation, I:E ratio, etc. Also, patients' breath triggering and cycling will not be accurate as the baseline flow depends on the accurate leak estimates. Additionally, as alarms are mostly based on the patient/ventilator data, patient safety can potentially be compromised.

What is needed in the art is a system and method for accurately estimating both intentional and unintentional leaks in flow generation systems.

SUMMARY OF THE INVENTION

In one embodiment, a method for accurate leak estimation in a flow generation system includes the steps of measuring a total flow through the flow generation system, measuring a pressure in the primary flow circuit of the flow generation system, determining when the measured pressure is within a predetermined threshold of EPAP, and calculating an intentional leak flowrate and an unintentional leak flowrate based on the relationship $Q_{FS}(t)=Q_{IL}(t)+Q_{UL}(t)$ when the measured pressure is within the predetermined threshold. In one embodiment, the total flow includes a first flow source comprising ambient air and a second flow source comprising pressurized oxygen. In one embodiment, the primary flow circuit comprises a flow sensor for measuring the total flow, an airflow generator and a patient interface connection. In one embodiment, $P_{PS}(t) \cong EPAP$ when $P_{PS}(t)$ is within 0.5 $cmH_2O$ from EPAP. In one embodiment, $P_{PS}(t) \cong EPAP$ when $P_{PS}(t)$ is within 0.2 $cmH_2O$ from EPAP. In one embodiment, $P_{PS}(t) \cong EPAP$ when $P_{PS}(t)$ is within 0.1 $cmH_2O$ from EPAP. In one embodiment, $P_{PS}(t) \cong EPAP$ when $P_{PS}(t)$ is within 1 $cmH_2O$ from EPAP. In one embodiment, the method includes the step of determining the intentional leak flow rate at least partially based on a selected patient interface orifice size. In one embodiment, the method includes the step of determining a flowrate of the lungs $Q_{IL}(t)$ by satisfying the equations:

$$Q_{FS}(t)=Q_{IL}(p,t)+Q_{UL}(p,t)+Q_L(t)$$

when $P_{PS}(t) \cong EPAP$, $$Q_{FS}(t)=Q_{IL}(t)+Q_{UL}(t)$$

$$Q_{UL}(p,t)=\alpha \cdot Q_{IL}(p,t)$$

In one embodiment, the method includes the step of determining a flowrate of the lungs $Q_L(t)$ by satisfying the equations:

$$Q_{FS}(t)=Q_{IL}(p,t)+Q_{UL}(p,t)+Q_L(t)$$

when $P_{PS}(t) \cong EPAP$, $$Q_{FS}(t)=Q_{IL}(t)+Q_{UL}(t)$$

In one embodiment, the method includes the step of modeling an orifice equation for a total leaks using an empirical equation. In one embodiment, the total flow includes a third flow source.

In one embodiment, a flow generation system includes an airflow generator connected in-line to a flow sensor, a pressure sensor and a patient interface connection by a first gas flow circuit; and a controller electrically coupled to the airflow generator, the flow sensor and the pressure sensor; where the airflow generator is configured to change speed based on a control signal received from the controller, the control signal based on a first flow value measured from the flow sensor and an unintentional leak flow value that is derived from a proportional relationship with a predetermined intentional leak flow value. In one embodiment, the intentional leak flow value is determined at least partially by a selected patient interface orifice size. In one embodiment, the control signal is at least partially driven by a flowrate value of the lungs $Q_L(t)$ that is determined by satisfying the equations:

$$Q_{FS}(t)=Q_{IL}(p,t)+Q_{UL}(p,t)+Q_L(t)$$

when $P_{PS}(t) \cong$ EPAP, $$Q_{FS}(t)=Q_{IL}(t)+Q_{UL}(t)$$

$$Q_{UL}(p,t)=\alpha \cdot Q_{IL}(p,t)$$

In one embodiment, $P_{PS}(t) \cong$ EPAP when $P_{PS}(t)$ is within 0.5 cmH$_2$O from EPAP. In one embodiment, the control signal is at least partially driven by a flowrate of the lungs $Q_L(t)$ that is determined by satisfying the equations:

$$Q_{FS}(t)=Q_{IL}(p,t)+Q_{UL}(p,t)+Q_L(t)$$

when $P_{PS}(t) \cong$ EPAP, $$Q_{FS}(t)=Q_{IL}(t)+Q_{UL}(t)$$

In one embodiment, $P_{PS}(t) \cong$ EPAP when $P_{PS}(t)$ is within 0.5 or other small pressure cmH$_2$O from EPAP. In one embodiment, $P_{PS}(t) \cong$ EPAP when $P_{PS}(t)$ is within 0.2 cmH$_2$O from EPAP. In one embodiment, $P_{PS}(t) \cong$ EPAP when $P_{PS}(t)$ is within 0.1 cmH$_2$O from EPAP. In one embodiment, $P_{PS}(t) \cong$ EPAP when $P_{PS}(t)$ is within 1 cmH$_2$O from EPAP. In one embodiment, an orifice equation for a total leaks value that is used to at least partially drive the control signal is modeled using an empirical equation. In one embodiment, the flow generation system includes a humidifier connected to the first gas flow circuit upstream of the patient interface connection and downstream of both the flow sensor and pressure sensor. In one embodiment, the airflow generator is an air pump. In one embodiment, the flow generation system is a ventilator. In one embodiment, the flow generation system includes a bacteria filter in-line with a second gas flow circuit, wherein the second gas flow circuit is connected to a first junction upstream of the patent interface connection and a second junction downstream of the flow sensor and pressure sensor. In one embodiment, the second gas flow circuit includes a check valve upstream of the bacteria filter. In one embodiment, the bacteria filter is part of a removable cartridge that comprises a portion of the first and second gas flow circuit. In one embodiment, the flow generation system includes a heat moisture exchanger and bacteria filter in-line with the first gas flow circuit upstream of the patient interface connection and downstream of the flow sensor and pressure sensor.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
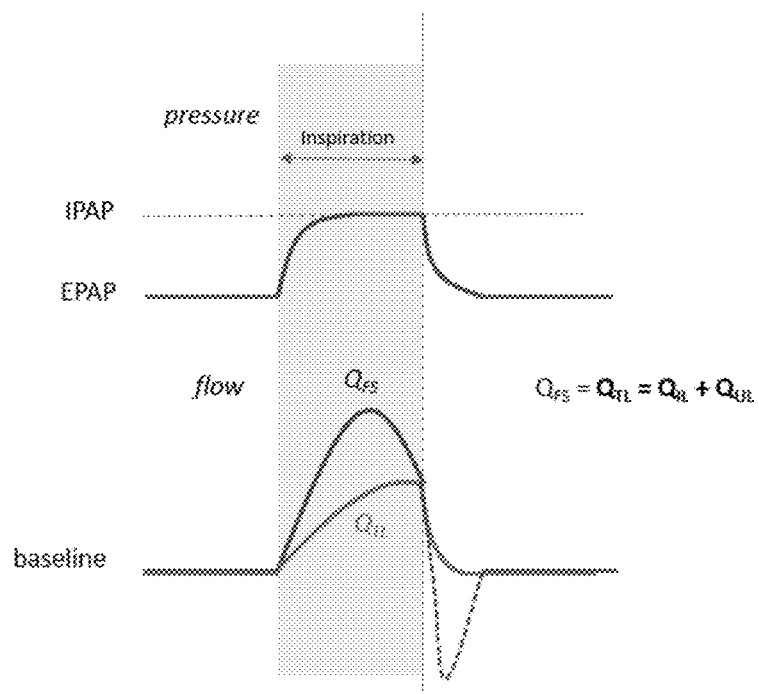
FIG. 1A is a graphical depiction of a method for finding total leak during mandatory mode for a system with intentional leak according to one embodiment.

It is to be understood that the figures and descriptions of the present invention have been simplified to illustrate elements that are relevant for a more clear comprehension of the present invention, while eliminating, for the purpose of clarity, many other elements found in systems and methods for accurately estimating both intentional and unintentional leaks in flow generation systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"P" as used herein means pressure.

"$P_{PS}$" as used herein means pressure as measured by the Pressure Sensor.

"PEEP" as used herein means Positive End Expiratory Pressure.

"Q" as used herein means flowrate.

"$Q_{FS}$" as used herein means flowrate as measured by the Flow Sensor.

"$Q_{IL}$" as used herein means flowrate at the Intentional Leak site.

"$Q_{UL}$" as used herein means flowrate at the Unintentional Leak site.

"$Q_L$" as used herein means flowrate at the Lungs.

"$Q_{TL}$" as used herein means Total Leak flowrate (i.e. $Q_{TL}=Q_{IL}+Q_{UL}$).

"EPAP" as used herein means Expiratory Positive Airway Pressure.

"$\alpha$" as used herein means coefficient.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are systems and methods for accurately estimating both intentional and unintentional leaks in flow generation systems.

Methods of leak estimation described herein include modeling leak in a function with some other aspect measurable in the system. The function or relationship is found at certain points when the leak flow can be safely assumed to be equal to the measured flow from the flow sensor. This can happen at several points from breath to breath. A primary difference between the methods described herein and conventional methods is that the methods described herein corrects the net patient flow throughout the breathing phase, i.e., during inspiration and exhalation. Thus, the device can accurately measure and compensate all leaks in real time, producing accurate patient and ventilator data such as tidal volume and minute volume. Additionally, patient/device synchrony is greatly enhanced due to the accurate real time leak compensation again throughout the breathing phase. Device alarms become accurate and reliable such that false positive or false negative alarms can be greatly reduced. Additionally, tighter alarm settings become possible, improving patient safety.

Generally, embodiments of the invention include methods to find leak based on the general concept of total leak=intentional leak+unintentional leak, and the necessary condition $Q_{FS}=Q_{TL}$. Total flow from the flow generator equals the total leak (both intentional and unintentional leaks) downstream of the flow generator. The corresponding $P_{PS}$ (pressure measured in the device) can be determined. There are a couple of general methods in finding $Q_{TL}$ and $P_{PS}$ with respect to the ventilation devices—one during inspiration and the other during exhalation. Flow waveform is affected by intentional leak, unintentional leak, mandatory mode, spontaneous mode. The total leak with intentional leak will be higher than the case without intentional leak. Typically, it's not as easy or practical to find $Q_{TL}$ or $P_{PS}$ during inspiration as the case during exhalation. However, it is possible to get $Q_{TL}$ or $P_{PS}$ during inspiration (Examples are shown in FIGS. 1A-1D). $Q_{TL}$ and $P_{PS}$ can be readily found during exhalation as long as the exhalation period is long enough to yield steady state condition, i.e., $Q_{FS}=Q_{TL}$.

Figure 1B:
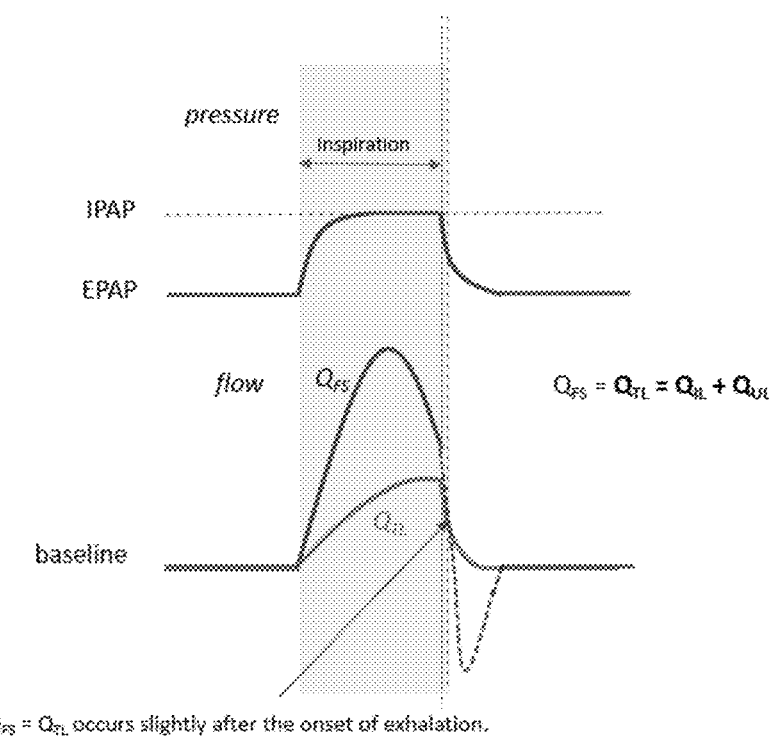
FIG. 1B is a graphical depiction of a method for finding total leak during spontaneous mode for a system with intentional leak according to one embodiment.
Figure 1C:
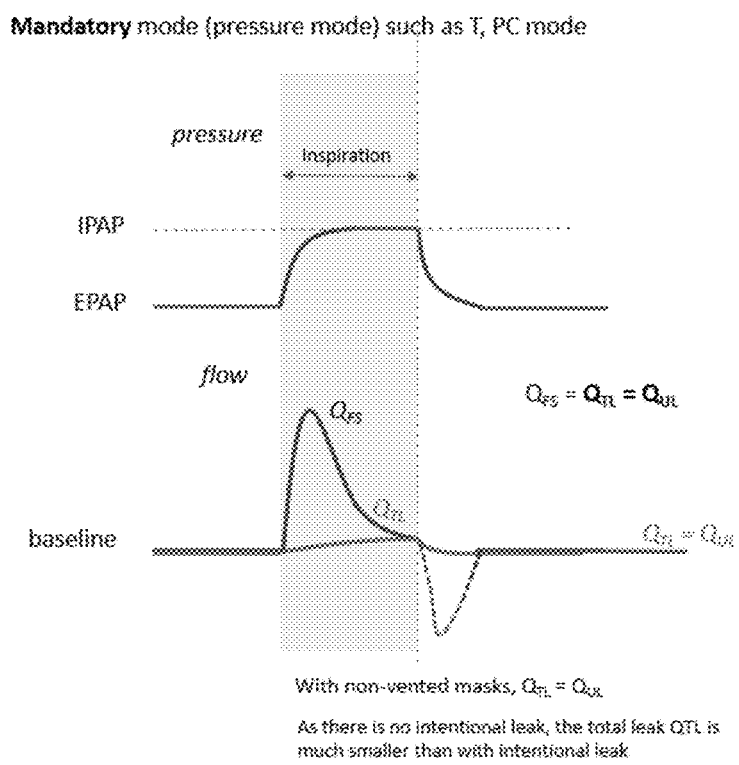
FIG. 1C is a graphical depiction of a method for finding total leak during mandatory mode for a system with no intentional leak according to one embodiment.
Figure 1D:
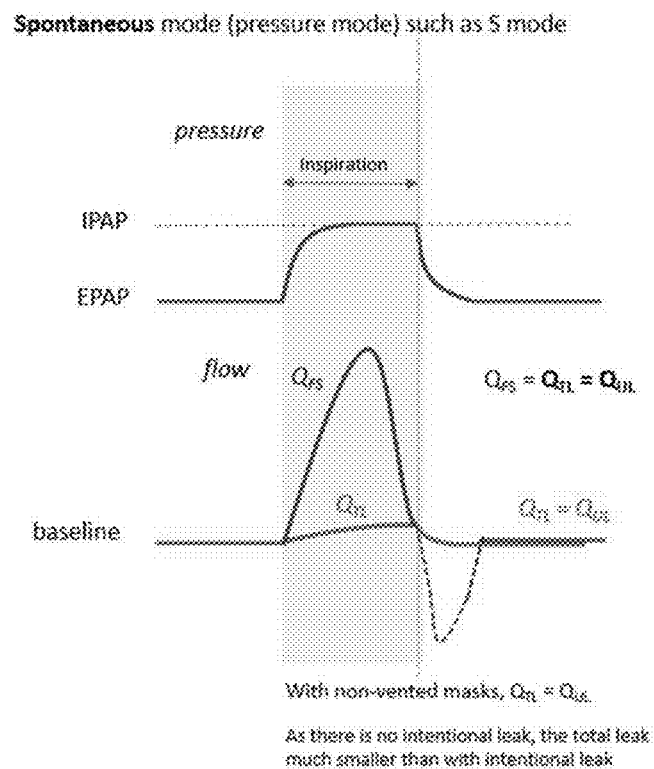
FIG. 1D is a graphical depiction of a method for finding total leak during spontaneous mode for a system with non-intentional leak according to one embodiment.
Figure 1E:
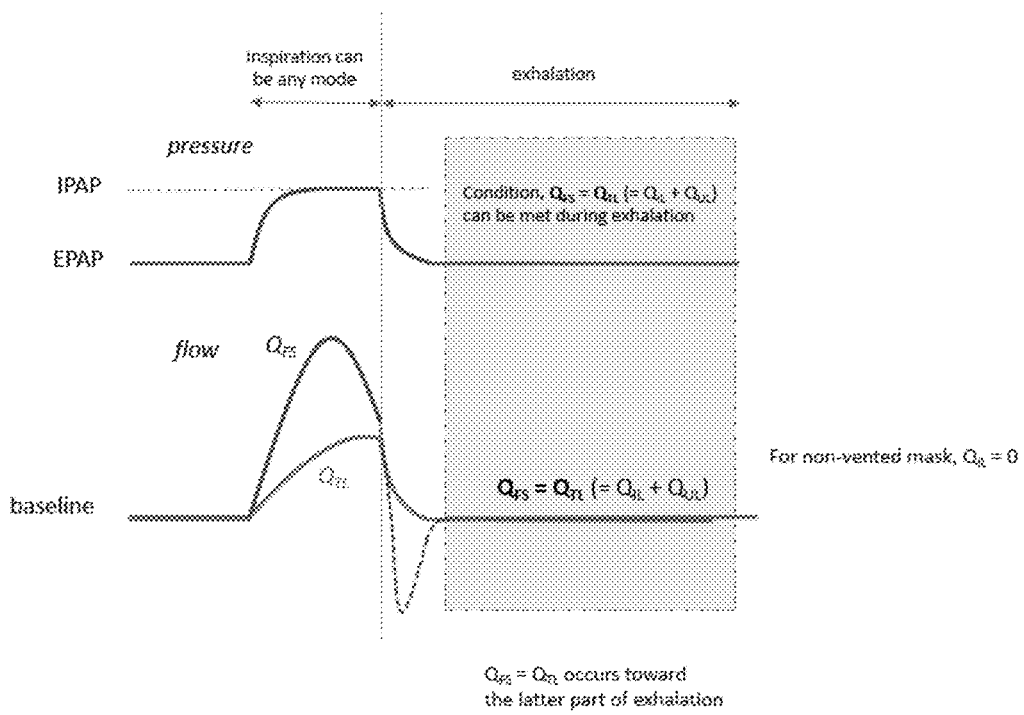
FIG. 1E is a graphical depiction of a method for finding total leak during mandatory or spontaneous mode for a system with intentional and/or no-intentional leaks according to one embodiment.

With reference now to FIG. 1A, during inspiration, with respect to intentional leak systems in mandatory mode, the machine delivers breaths to the patient. Toward the end of inspiration, $Q_{FS}$ and $Q_{TL}$ start to converge. When $Q_{FS}$ and $Q_{TL}$ are equal, $Q_{TL}$ and $P_{PS}$ can be determined. With reference now to FIG. 1B, in spontaneous mode, the patient triggers breaths and exhalation starts when exhalation criteria are met. Depending on the exhalation criteria, though $Q_{FS}$ and $Q_{TL}$ start to converge toward the end of inspiration, they may not be equal during inspiration. However, $Q_{FS}$ and $Q_{TL}$ will meet during the first part of exhalation. As the pressure decreases during the first part of exhalation, $Q_{TL}$ and $P_{PS}$ can be determined. For a system with no intentional leak, with reference now to FIG. 1C, in mandatory mode, the machine delivers breaths to the patient. Toward the end of inspiration, $Q_{FS}$ and $Q_{TL}$ (or $Q_{UL}$ as $Q_{IL}=0$) start to converge. When $Q_{FS}$ and $Q_{TL}$ are equal, $Q_{TL}$ and $P_{PS}$ can be selected. With reference now to FIG. 1D, in spontaneous mode, the patient triggers breaths and exhalation starts when exhalation criteria are met. Depending on the exhalation criteria, though $Q_{FS}$ and $Q_{TL}$ start to converge toward the end of inspiration, they may not be equal during inspiration. However, $Q_{FS}$ and $Q_{TL}$ will meet during the first part of exhalation. As the pressure decreases during the first part of exhalation, $Q_{TL}$ and $P_{PS}$ can be determined. With reference now to FIG. 1E, during exhalation phase, the algorithm applies to both intentional and non-intentional leaks, e.g., vented and non-vented masks. It also applies to both mandatory and spontaneous modes. The algorithm is applicable at EPAP or PEEP.

Figure 1F:
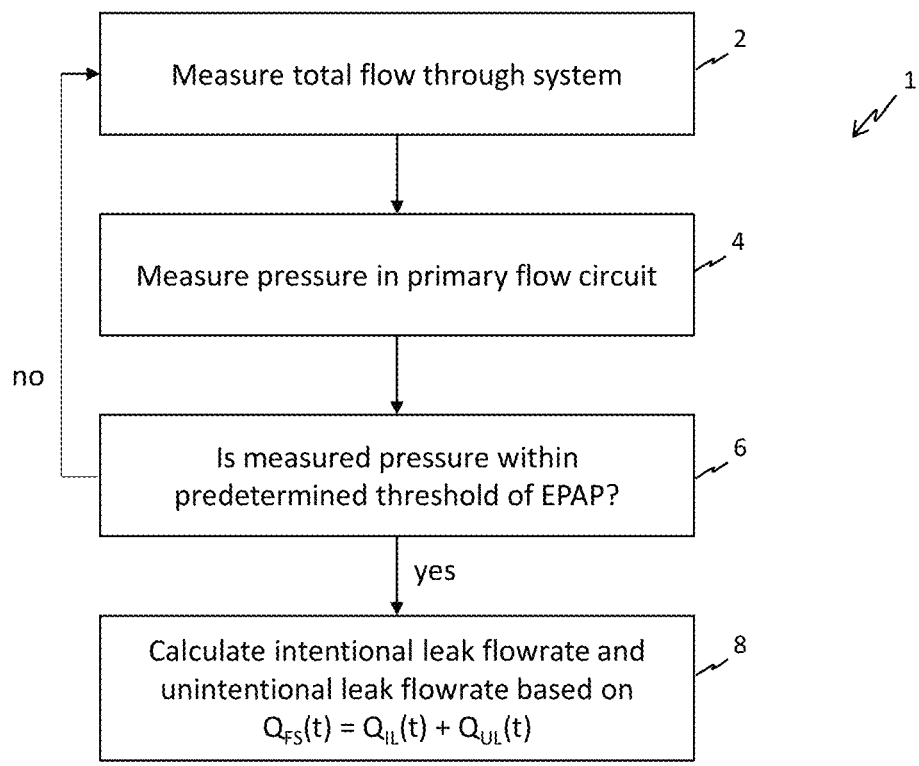
FIG. 1F is a flow chart of a method for leak estimation in a flow generation system according to one embodiment.

With reference now to FIG. 1F, in one embodiment, a method 1 for accurate leak estimation in a flow generation system is described. A total flow is measured through the flow generation system 2, and a pressure is measured in in the primary flow circuit of the flow generation system 4. The system then determines when the measured pressure is within a predetermined threshold of EPAP 6, and calculates an intentional leak flowrate and an unintentional leak flowrate based on the relationship $Q_{FS}(t)=Q_{IL}(t)+Q_{UL}(t)$ when the measured pressure is within the predetermined threshold 8. The total flow can include a first flow source such as ambient air and a second flow source such as pressurized oxygen. A third flow source, such as another gas source can also be connected to the system and factored into the total flow. In one embodiment, the total flow includes a third flow source. In one embodiment, the primary flow circuit includes a flow sensor for measuring the total flow, an airflow generator and a patient interface connection. In certain embodiments, the primary flow circuit is the conduit or system of conduits connecting the airflow generator to the patient interface connection. System embodiments can have numerous configurations, just some of which are described below as exemplary embodiments.

Figure 2:
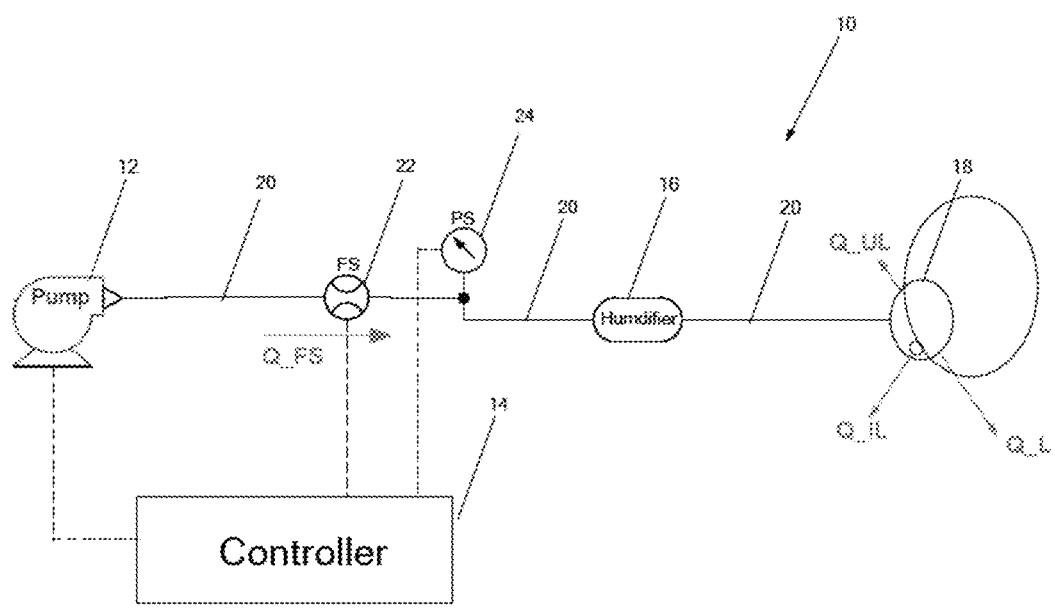
FIG. 2 is a diagram of a flow generation system circuit according to one embodiment.

Embodiments of the invention utilize techniques including orifice modelling, pressure vs. flow characteristics, and real time application of P vs Q characteristic to measured pressure/flow in systems and methods for accurately estimating both intentional and unintentional leaks in flow generation systems. With reference now to FIG. 2, a flow generation system is shown in one embodiment as a ventilator circuit 10 represented in the pneumatic schematic circuit diagram. An air pump 12 is connected via an in-line gas flow circuit 20 to a humidifier 16 and a patient interface 18. The patient interface 18 can include tubing such as single-limb flexible patient tubing and a patient interface for the patient to breathe through. In this embodiment, the patient interface 18 includes a facemask connected to a flexible tubing that extends to the gas flow circuit 20. A flow sensor 22 and a pressure sensor 24 are positioned in the gas flow circuit 20 between the air pump 12 and the humidifier 16, and they communicate measurements to a controller 14 that controls the air pump 12.

In one embodiment according to a first method:

$$Q_{FS}(t)=Q_{IL}(p,t)+Q_{UL}(p,t)+Q_L(t) \quad (1)$$

$$\text{when } P_{PS}(t) \cong \text{EPAP,} \quad (2)$$

$$Q_{FS}(t)=Q_{IL}(t)+Q_{UL}(t) \quad (3)$$

$$Q_{UL}(p,t) = \propto \cdot Q_{IL}(p,t) \quad (4)$$

where $Q_{FS}(t)$ is measured and $Q_{IL}(p,t)$ is calibrated. $Q_{UL}(p,t)$ can be derived from $Q_{IL}(p,t)$, consequently $Q_L(p,t)$ can be derived. Equation 4 assumes that $Q_{UL}$ has a proportional relationship with $Q_{IL}$. $\propto$ is the coefficient that describes the proportionality. During no breathing ($P_{PS}(t) \cong$ EPAP) equation 3 is true because $Q_L=0$. In certain embodiments, $P_{PS}(t) \cong$ EPAP when $P_{PS}(t)$ is within 0.5 cmH$_2$O from EPAP. In one embodiment, $P_{PS}(t) \cong$ EPAP when $P_{PS}(t)$ is within 0.2 cmH$_2$O from EPAP. In one embodiment, $P_{PS}(t) \cong$ EPAP when $P_{PS}(t)$ is within 0.1 cmH$_2$O from EPAP. In one embodiment, $P_{PS}(t) \cong$ EPAP when $P_{PS}(t)$ is within 1 cmH$_2$O from EPAP. $\propto$ can be found by substituting equation 4 into equation 3. $Q_{IL}$ is known to the device because it has been previously calibrated against the pressure of the system for known user interfaces, i.e., orifice size. The $\propto$ found during this phase of the breathing cycle is then used to calculate $Q_{UL}$ until the next breath and a new $\propto$ is found with when breath condition is met. Once $Q_{UL}$ has been estimated, $Q_L$ can be determined using equation 1. Since $\propto$ is reevaluated each breath, this will ensure leak compensation from breath to breath at each sampling cycle.

Figure 3A:
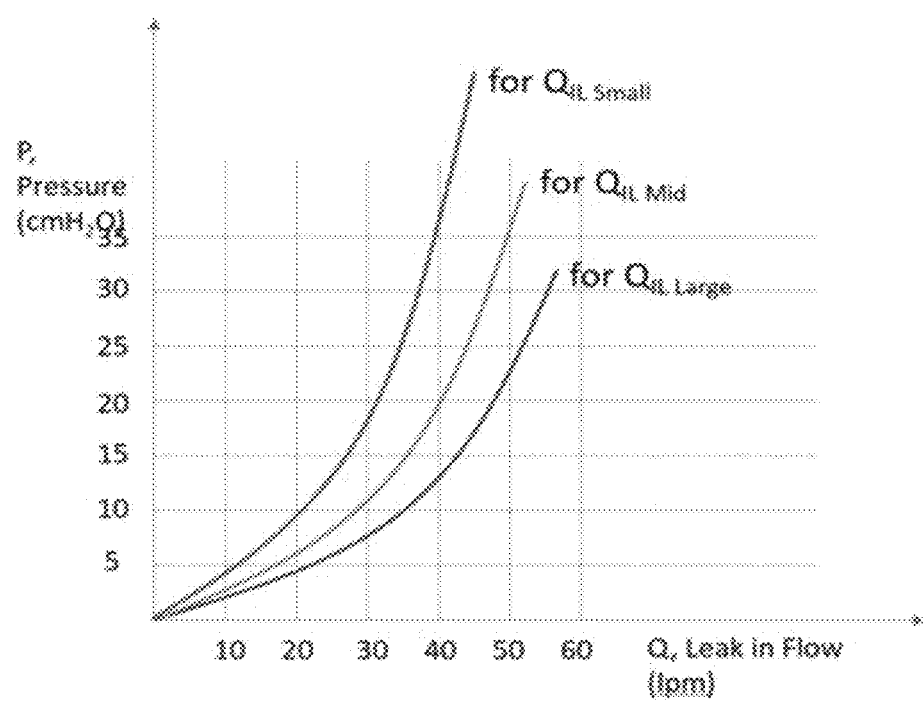
FIG. 3A is a graphical curve fit relationship between $Q_{FS}$ and $P_{PS}$ according to one embodiment.

An exemplary $Q_{IL}$ graph is shown in FIG. 3A, i.e., a family of $Q_{IL}$ covering the entire range of orifice size (aka known leaks) at each pressure is obtained from calibration. In the example of FIG. 3A, three representative calibration data are shown.

In one embodiment according to a second method:

$$Q_{FS}(t)=Q_{IL}(p,t)+Q_{UL}(p,t)+Q_L(t) \quad (1)$$

$$\text{when } P_{PS}(t) \cong \text{EPAP,} \quad (2)$$

$$Q_{FS}(t)=Q_{IL}(t)+Q_{UL}(t) \quad (4)$$

where $Q_{FS}(t)$ is measured & $Q_{IL}$ (p) is calibrated. $Q_{UL}(p)$ can be modeled from pre-calibrated family of Q vs. P chart. Consequently $Q_L(p,t)$ can be derived from equation 2. In one embodiment, $Q_{UL}(p)$ is derived from a pre-calibrated family of Q vs. P chart or a lookup table. P vs. Q relationship can be easily obtained via interpolation/extrapolation of the data (see for example FIG. 3A). In one embodiment, $Q_{UL}(p)$ is derived from a curve fit equation. Similar to the above P vs. Q picture, instead of saving the P vs. Q relationship in lookup table, the same information can be saved as polynomial equations via curve-fit method. Once representative set of curve-fitted polynomial equations are saved, all other data can then be obtained via interpolation/extrapolation of the existing data.

In one embodiment according to a third method:

$$Q_{FS}(t)=Q_{IL}(p,t)+Q_{UL}(p,t)+Q_L(t) \quad (1)$$

$$\text{when } P_{PS}(t) \cong \text{EPAP,} \quad (2)$$

$$Q_{FS}(t)=Q_{IL}(t)+Q_{UL}(t) \quad (4)$$

the orifice equation for total leaks, i.e., $Q_{TL}$ (p)=$Q_{IL}$ (p)+$Q_{UL}$ (p) can be modeled in one embodiment using (but not limited to) the following equations:

$$P_{PS}(t)=7.57 \times 10^4 Q_{TL}(t)^{1.85} L/(D^5 P_{abs}) \text{ (Empirical)} \quad (5)$$

$$\text{or } P_{PS}(t)=8 f \rho Q_{TL}(t)^2 L/(D^5 \pi^2) \text{ (Darcy Weisbach)} \quad (6)$$

Now, $Q_{TL}$ (p) can be determined. The total leak opening can be characterized as an orifice. Using equations 5 and 6, the total leak orifice's diameter can be estimated during no breathing ($P_{PS}(t) \cong$ EPAP). The diameter value calculated during this phase of the breathing cycle is captured and then applied back to the equation 5 and 6 to find the $Q_{TL}$ throughout the breath (including when $P_{PS}(t) \neq$ EPAP). $Q_{TL}$ (t) can be an average value between the values calculated from the two equations, (5) and (6). During the next breath, when the condition is met, i.e., (2), the orifice diameter will be estimated again to ensure that any changes in the patient interface is accounted for.

In certain embodiments, the third method can run in the background all the time in conjunction with either the first or second method. The leak compensation can be verified from other methods, such as the first or second method. In certain embodiments, the third method can point out incorrect mask (user interface) selection if this option is available. If there is no $Q_{UL}$, the total leak estimated from the third method can be compared to the known $Q_{IL}$ of the selected mask. From the comparison, the system can tell whether the correct mask was selected. In the embodiments, the third method by itself would be sufficient to yield $Q_L$ for various configurations.

Figure 3B:
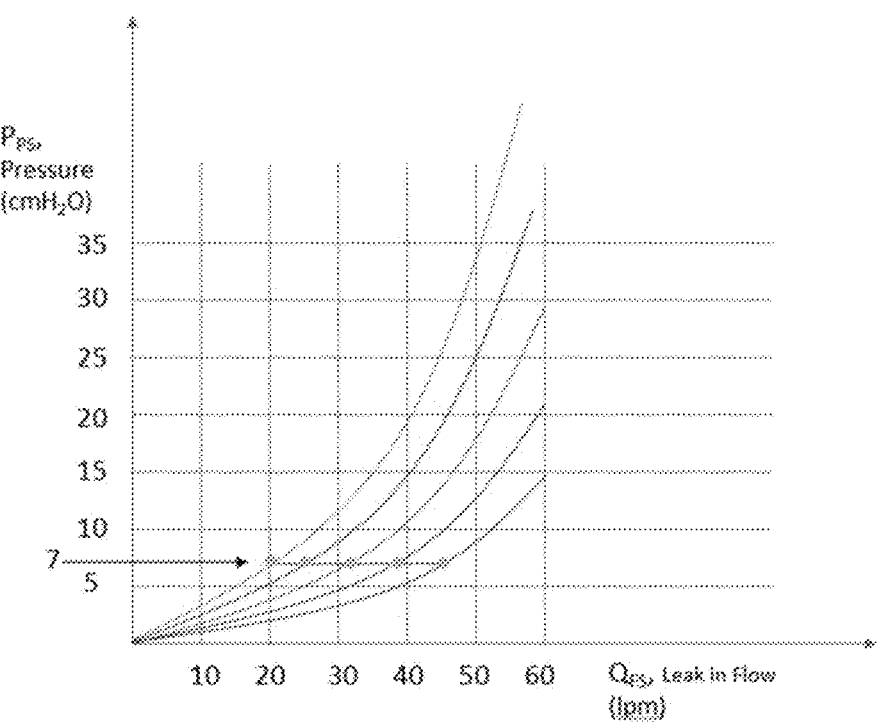
FIG. 3B is a graphical curve fit relationship between $Q_{FS}$ and $P_{PS}$ according to another embodiment.

In certain embodiments, the leak characteristics can be formulated as defined area size, the functional relationship between $Q_{FS}$ and $P_{PS}$, a tabulated (e.g. lookup table) relationship between $Q_{FS}$ and $P_{PS}$, or a curve fit relationship between $Q_{FS}$ and $P_{PS}$. Defined area size can be possibly in the orifice, or any other shape. The total leak can be formulated more commonly as an orifice. However, the total leak can take the form of other configurations such as square, octagon, etc. Regarding the functional relationship between $Q_{FS}$ and $P_{PS}$, the total leak also can be represented as mapping between $Q_{FS}$ and $P_{PS}$. This can include non-linear relationships including fuzzy-logic type expert system. This relies on known knowledge—either empirical or theoretical. A tabulated relationship i.e. lookup table or other forms of tabulated relationship can also be employed. Alternatively, combinations of lookup table and functional relationship or other methods can be beneficial as these can expedite the sampling process and yield the desirable result faster. A curve fit relationship between $Q_{FS}$ and $P_{PS}$ can be utilized as shown for example in FIG. 3B. In this example, if the corresponding pressure is 7 ($P_{PS}$) when $Q_{FS}=Q_{TL}$ condition is met, appropriate curve-fit can be either created or selected from previously generated plots shown above. For example, if $Q_{FS}=25$ lpm at $P_{PS}=7$, then the second plot (red) from the left will be selected. This example is for illustration purpose only, as the actual relationship between $Q_{FS}$ and $P_{PS}$ can be quite different. In certain embodiments, an empirical formula such as $P_{PS}(t)=7.57\times10^4\ Q_{TL}(t)^{1.85}\ L/(D^5\ P_{abs})$(Empirical) or $P_{PS}(t)=8\ f\ \rho\ Q_{TL}(t)^2\ L/(D^5\ \pi^2)$ (Darcy Weisbach) can be employed.

The methods described herein are compatible with various system configurations. For example, embodiments of systems may include a humidifier that is either an internal or external humidifier. In certain embodiments, systems have an internal exhalation valve. In certain embodiments, system have an external exhalation valve with an exhalation flow sensor. In certain embodiments, system have an external exhalation valve without an exhalation flow sensor but with known control mechanism. The patient interface in certain embodiments may be a nasal mask, full face mask, pillow mask, cannula, trach tube, endotracheal tube, etc. Thus, various patient interfaces with or without intentional leak can be utilized. Interfaces can include both vented and non-vented masks/patient interfaces, and both Single limb and dual limb systems. Single limb with and without intentional leak with various patient interface and with or without external exhalation valve, dual limb with and without intentional leak with various patient interface and with or without external exhalation valve. Interfaces may or may not have an internal exhalation valve. Embodiments of the leak detection algorithm apply to virtually all combinations of leaks, patient interface, components such as exhalation valve, etc.

Figure 4:
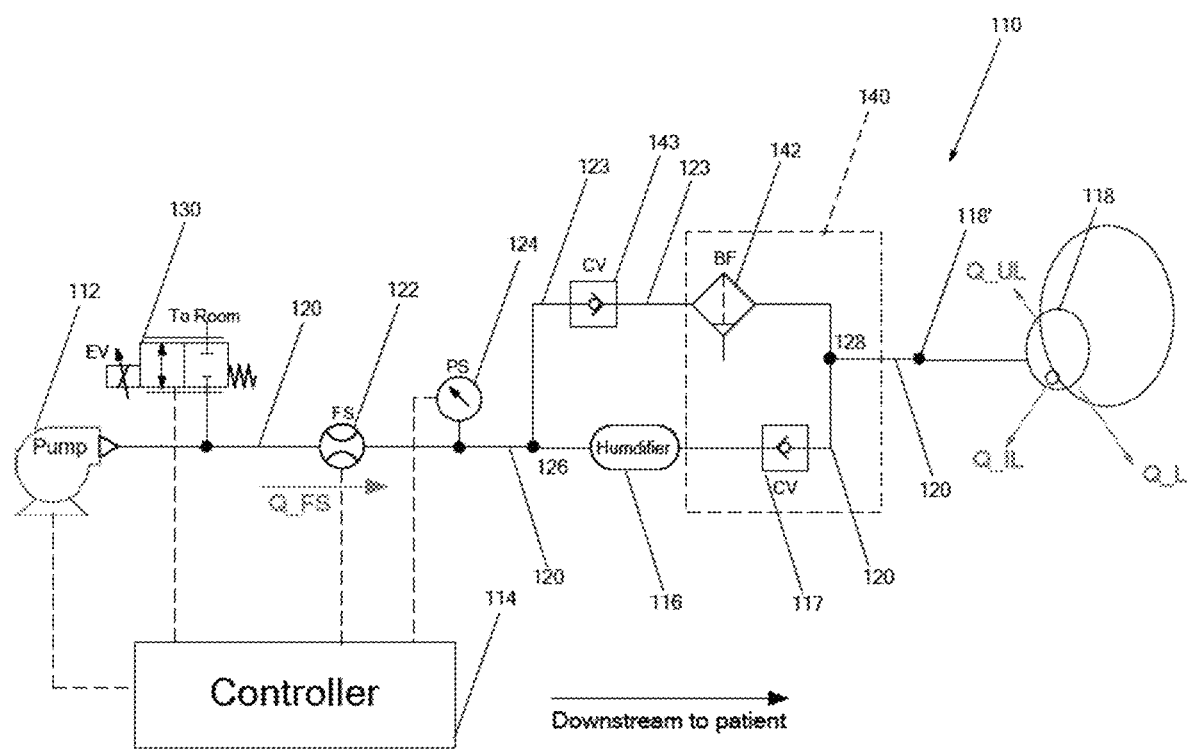
FIG. 4 is a diagram of a flow generation system circuit according to one embodiment.

As shown in the system pneumatic schematic circuit of FIG. 4, the system 100 according to one embodiment includes an airflow generator 112 connected in-line to a humidifier 116, a first check valve 117 and a patient interface 118. These components are connected by a first gas flow circuit 120, which in certain embodiments, can be formed by openings or rigid tubular structures defined by the system housing(s), connections by flexible tubing, or a combination of both. In certain embodiments, the humidifier is replaced by an empty chamber or a void. The airflow generator 112 can be of types known in the art, such as blowers, fans, or pressure generators. In certain embodiments, the check valve is a resilient one-way valve, such as a duckbill valve. The check valve can also be a 2-way valve this is electronically controlled by the controller 114 or a pneumatically piloted 2-way valve. The first check valve 117 is configured to restrict the upstream flow of gas. The second check valve 143 is configured to restrict the downstream flow of gas. A controller 114 is wired to the pump, and it sends drive signals to the pump during operation. The controller 114 can store program or historical data for controlling the breathing patterns of the patient. The controller 114 can also relay calculate drive signals for the air pump and valves within the system, based on programed software and/or feedback from sensors in the system. A cartridge 140 houses part of the first gas flow circuit 120, the first check valve 117 and the bacterial filter 142. The cartridge 140 also houses part of the second gas flow circuit 123. A second gas flow circuit 123 connects a second check valve in-line with the bacterial filter. The cartridge 140 is installed downstream of a first junction 126 located upstream of the humidifier 116, and the cartridge 140 includes a second junction 128 located downstream of the humidifier 116, the cartridge further including the first check valve 117. The branch of the second gas flow circuit 123 including the second check valve 143 and the bacterial filter 142, extending between the first junction 126 and the second junction 128 may be referred to as the exhalation circuit in certain embodiments. The branch of the first gas flow circuit including the humidifier 116 and the first check valve between the first junction 126 and the second junction 128 may be referred to as the inhalation circuit in certain embodiments.

Figure 5:
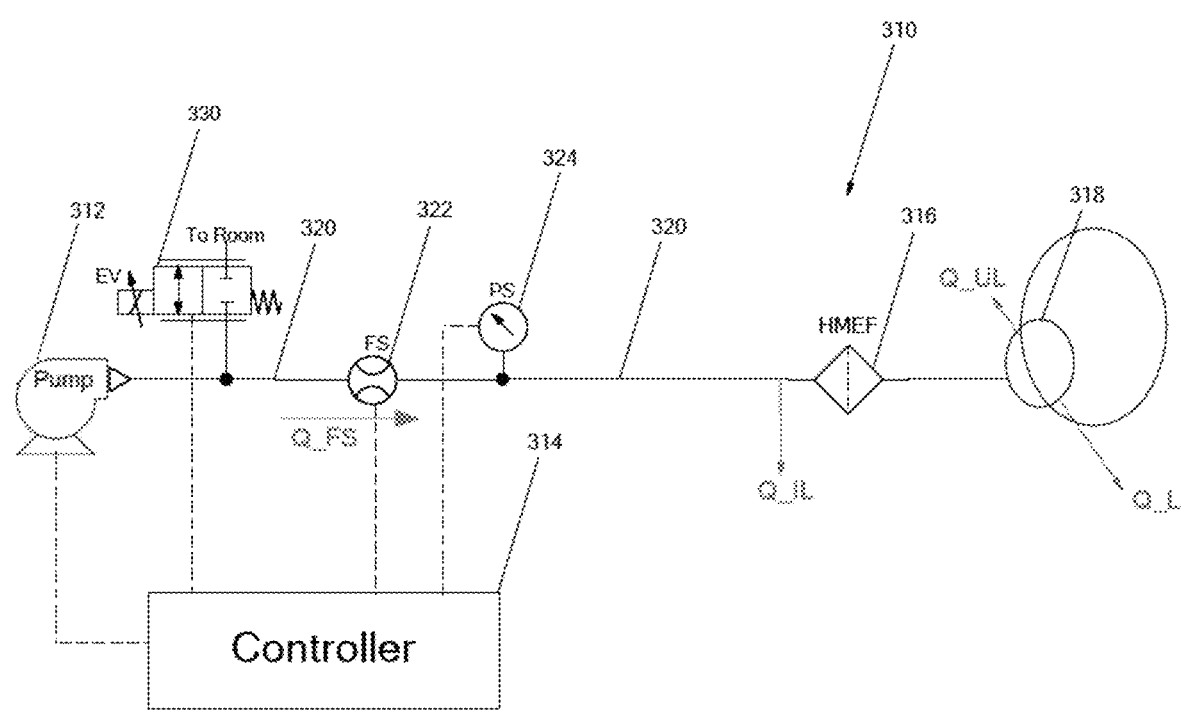
FIG. 5 is a diagram of a flow generation system circuit according to one embodiment.

Junctions 126 and 128 may be open junctions that allow the free flow of gas throughout the connected gas lines at the junctions. In certain embodiments, one or both of the junctions 126, 128 are 3-way valves that can be controlled electronically via the controller 114, pneumatically piloted or actuated by a pressure gradient during inspiration and exhalation. In certain embodiments, if a 3-way valve is used at a junction 126, 128, the redundant first and/or second check valves 117, 143 can be removed. If the second junction 128 uses a three way valve, it can optionally be housed within the cartridge 140. The second check valve 143 can optionally be included within the cartridge 140. In one embodiment, a junction valve is located at the second junction 128. In certain embodiments, the junction valve is configured to limit or block gas access to a particular branch of the junction when gas transfer to that branch is not desired. For example, in one embodiment, a junction valve located at the second junction 128 has a first position during an inhalation phase, blocking the downstream gas flow to the bacteria filter 142, and a second position during an exhalation phase, blocking downstream gas flow to the humidifier 116. Similarly, and in addition, a junction valve can be located at junction 128 that has a first position during an inhalation phase, blocking upstream gas flow to the bacteria filter, and a second position during exhalation, blocking upstream access to the humidifier. In this case, the junction valve can be housed within the cartridge. The junction valve can be a flexible pressure actuated check valve, or an actuating valve that communicates with the controller 114 for receiving control signals to open or close corresponding with inhalation and exhaustion. In certain embodiments, the patient interface 118 includes a connection port 118' and the flexible tubing, mask and/or mouthpiece that the patient breathes directly into. In certain embodiments, the patient interface includes masks (e.g. nasal, full, total, pillow, or combinations of these), a mouth piece, an endotracheal tube or a tracheostomy tube. The patient interface 118 may or may not have intentional leakage. The cartridge 140 is a removable cartridge that includes a bacteria filter 142 connected-in line to the second check valve 143. The cartridge 140 is constructed of materials such as medical grade plastics that are capable of withstanding high temperature sterilization, are autocleaveable, or are similar of withstanding some type of sterilization or autoclaving chamber. As shown in the circuit of FIG. 5, the position of the cartridge 140 prevents cross-contamination between patients via the bacterial filter by preventing the return of contaminated air back to the main body of the ventilator components such as the airflow generator 112. In certain embodiments where a junction valve is used, patient exhaled gas is prevented from returning to the main body of the ventilator, and can optionally be vented out to atmosphere. The position of the cartridge 140 also makes it simple to be replaced between patients.

In one embodiment, the system 100 includes an exhalation valve 130 wired to the controller 114 and connected to the gas flow circuit 120 downstream of the airflow generator 112 and upstream of the humidifier 116. The exhalation valve 130 can in certain embodiments be one of a voice coil actuator, stepper motor valve, proportional solenoid valve or a pneumatically piloted balloon valve. The exhalation valve 130 receives a signal from the controller 114 to open or shut, and can also receive an instruction for partially opening. In certain embodiments, the exhalation valve 130 is located at the first junction 126, between the first junction 126 and the second check valve 143, or between the second check valve 143 and the bacterial filter 142. In certain embodiments, the first junction 126 is eliminated when the exhalation valve 130 is located along the exhalation circuit 123. A second exhalation valve or leak port for passive exhalation can be located at the first junction 126, between the first junction 126 and the second check valve 143, or between the second check valve 143 and the bacterial filter 142. Some or all of the bacterial filter 142, second check valve 143, exhalation valve 130 and an exhalation leak port can be implemented as a single component. One or more flow sensors 122 and pressure sensors 124 can be present within the gas flow circuit 120. In one embodiment, a flow sensor 122 is wired to the controller 114 and connected to the gas flow circuit 120 downstream of the pump 112 and upstream of the humidifier 116. A flow sensor can be placed along the exhalation circuit 123 for embodiments where the exhalation valve 130 is placed along the exhalation circuit (e.g. after the exhalation valve 130 when the exhalation valve 130 is between the second check valve 143 and the bacterial filter 142). In one embodiment, a pressure sensor 124 is wired to the controller 114 and connected to the gas flow circuit 120 downstream of the pump 112 and upstream of the humidifier 116. The flow and pressure sensors can receive measurements that indicate and measure events such as pump airflow, exhalation airflow, pump pressure, exhalation pressure, etc. The controller 114 can use these measurements to control airflow and exhalation levels accordingly, based on the desired treatment begin administered to the patient.

Figure 6:
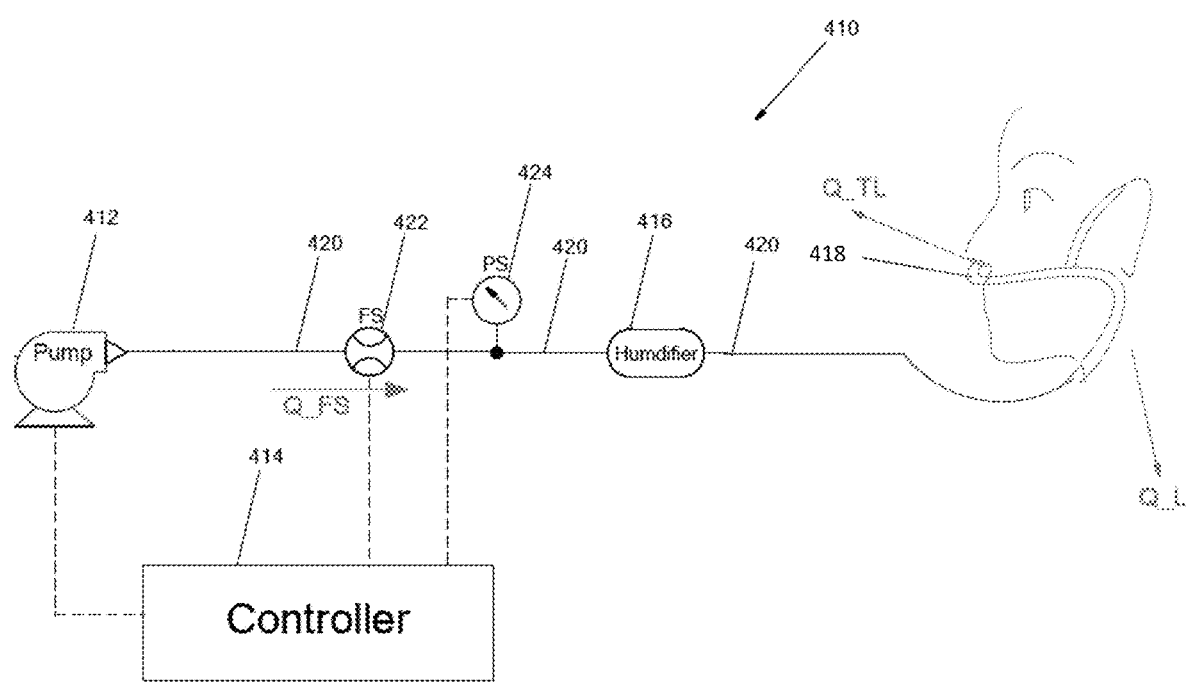
FIG. 6 is a diagram of a flow generation system circuit according to one embodiment.

Alternate embodiments of system configurations are shown in FIGS. 5 and 6. With reference now to FIG. 5, a flow generation system 310 is represented in the pneumatic schematic circuit diagram. An air pump 312 is connected via an in-line gas flow circuit 320 to a HMEF 316 and a patient interface 318. HMEF stands for Heat Moisture Exchanger and (Bacteria) Filter. HME is a simplest form of "humidification" by preventing moisture from escaping from the patient while breathing out. HMEF is a single device with HME and bacteria filter. As the intentional leak port is located upstream of the HMEF, i.e., away from the patient, patients can breathe in and out without losing moisture. Additionally, the device performance and patient comfort will be further improved with the presence of the exhalation valve. This embodiment eliminates the need of 100 cross-contamination mechanism. With the addition of 330 Exhalation valve, the breathing performance will be enhanced.

The patient interface 318 can include tubing that connects to the gas flow circuit 420 and an interface such as a facemask for the patient to breathe through. A flow sensor 322 and a pressure sensor 234 are positioned in the gas flow circuit 320 between the air pump 312 and the HMEF 316, and they communicate measurements to a controller 314 that controls the air pump 312. There are many clinical and commercial benefits with this embodiment. For example, as an in-line heated humidifier is not needed, the size can be smaller and the unit can be made mobile.

In the embodiment of FIG. 6, a flow generation system 410 is shown in the pneumatic schematic circuit diagram. An air pump 412 is connected via an in-line gas flow circuit 420 to a humidifier 416 and a patient interface 418. In this embodiment, the patient interface 418 includes a High Flow Nasal Therapy (HFNT) System connected to a flexible tubing that extends to the gas flow circuit 20. A flow sensor 422 and a pressure sensor 424 are positioned in the gas flow circuit 420 between the air pump 412 and the humidifier 416, and they communicate measurements to a controller 14 that controls the air pump 412.

Advantageously, the leak compensation algorithm opens up many possibilities. It makes the HFT devices compatible with wide range of patient interfaces (nasal cannula, all mask types and any existing and future patient interfaces), it makes it possible to monitor vital patient and ventilator data, it enables implementing various delivery modes which are not possible with other existing devices, and it expands the ability to add alarms.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 7:
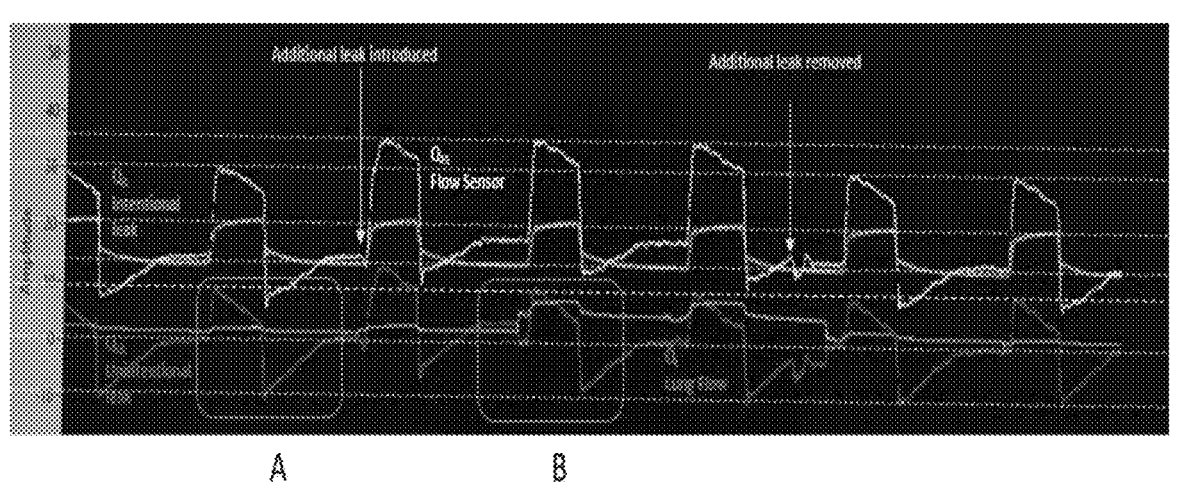
FIG. 7 is a graph showing an experimental lung flow $Q_L$ relative to leak that is introduced according to one example.

With reference now to FIG. 7, following an example tracking the first method described above, the graph shows intentional leak, unintentional leak, flow sensor measurement and lung flow. The algorithm works as follows: a user selects the patient interface type to provide $Q_{IL}(p)$ data to the algorithm.

$$Q_{FS}(t) = Q_{IL}(p,t) + Q_{UL}(p,t) + Q_L(t)$$

when $P_{PS}(t) \cong$ EPAP, $Q_{UL}(p,t) = \alpha \cdot Q_{IL}(p,t)$ e.g., at $t=t_1$ for $P_{PS}(t_1) = 10$ cmH$_2$O near the end of exhalation where $Q_{FS}(t)$ is measured and $Q_{IL}(p)$ is from pre-calibrated (see FIG. 3) data.

$Q_{UL}(p=10, t_1) = \alpha \cdot Q_{IL}(p=10, t_1)$ where $Q_{IL}(p=10, t_1)$
 $= 30$ lpm (from picture A)

and from $Q_{FS}(t_1) = Q_{UL}(p,t_1) + Q_{IL}(p,t_1)$ and $Q_L(t_1) = 0$ $Q_{UL}(p,t_1) = Q_{FS}(t_1) - Q_{IL}(p,t_1) = 40 - 30 = 10$ lpm where
 $Q_{FS}(t_1) = 40$ lpm (measured at $t_1$)

Then, $\alpha = Q_{UL}(p,t_1)/Q_{IL}(p,t_1) = 10/30 = 1/3$

This $\alpha$ is used for other pressure as well.

$$Q_{FS}(t) = Q_{IL}(p,t) + \alpha \cdot Q_{IL}(p,t) + Q_L(t)$$

Or $Q_L(t) = Q_{FS}(t) - Q_{IL}(p,t) - \alpha \cdot Q_{IL}(p,t)$

Or $Q_L(t) = Q_{FS}(t) - (1+\alpha) \cdot Q_{IL}(p,t)$

Condition:
$Q_{IL}(p)$ are pre-calibrated. User inputs this information, i.e., $Q_{IL}(p)$ is known to the device.

Advantageously, as shown in FIG. 7, $Q_L$ is not affected by an additional leak—whether introduced or removed, i.e., $Q_L$ in A and B are not affected by an additional leak.

Figure 8:
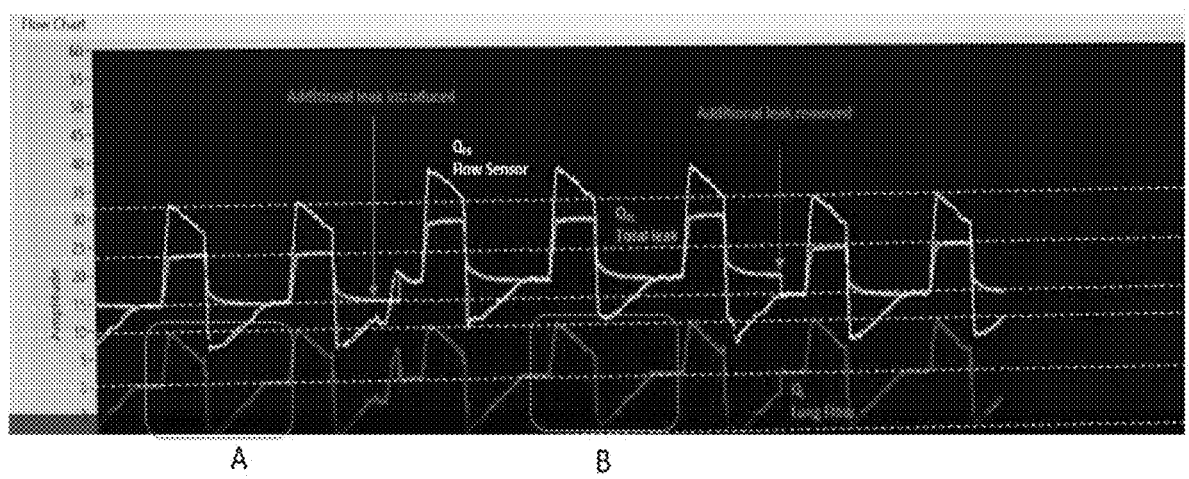
FIG. 8 is a graph showing an experimental lung flow $Q_L$ relative to leak that is introduced according to one example.

With reference now to FIG. 8, the graph shows total leak, flow sensor measurement and lung flow. In this example, the following is assumed:

$Q_{FS}$ Flow at Flow Sensor
$Q_{IL}$ Intentional Leak
$Q_{UL}$ Unintentional Leak
$Q_{IL}$ Lung
$Q_{TL}$ Total Leak = $Q_{IL} + Q_{UL}$
Q stands for flowrate
$P_{abs}$ absolute pressure
EPAP Expiratory Positive Airway Pressure
ρ (density of gas) constant 1.22
F constant 0.045 (empirically derived)
α coefficient
D diameter of orifice
L length of patient tube, e.g., 6 ft Tracking the third method described above, the algorithm works as follows:

$$Q_{FS}(t) = Q_{IL}(p,t) + Q_{UL}(p,t) + Q_L(t)$$

when $P_{PS}(t) \cong \text{EPAP}$, $Q_{FS}(t) = Q_{IL}(t) + Q_{UL}(t)$

Model the orifice equation for total leaks, i.e., $Q_{TL}(p) = Q_{IL}(p) + Q_{UL}(p)$ Using (but not limited to) the following two equations:

$$P_{PS}(t) = 7.57 \times 10^4 Q_{TL}(t)^{1.85} L/(D^5 P_{abs})$$ (Empirical equation)

$$P_{PS}(t) = 8f\rho Q_{TL}(t)^2 L/(D^5 \pi^2)$$ (from Darcy Weisbach)

Now, $Q_{TL}(p)$ can be determined.

Note that $Q_{TL}(p)$ can be determined via 1 or 2 above. Or $Q_{TL}(p)$ can also be determined by a combination of 1 & 2—taking average or weighted average method.

Also, method three can run in the background all the time in conjunction with either method one or method two to verify the leak compensation from other methods, i.e., one and two. Method three can point out incorrect mask (i.e., $Q_{IL}(p)$, user interface) selection if this option is available. Method three by itself would be sufficient to yield $Q_{IL}(p)$ for many configurations. Advantageously, as shown in FIG. 8, $Q_{IL}$ is not affected by an additional leak—whether introduced or removed, i.e., $Q_L$ in A and B are not affected by an additional leak.

Figure 9:
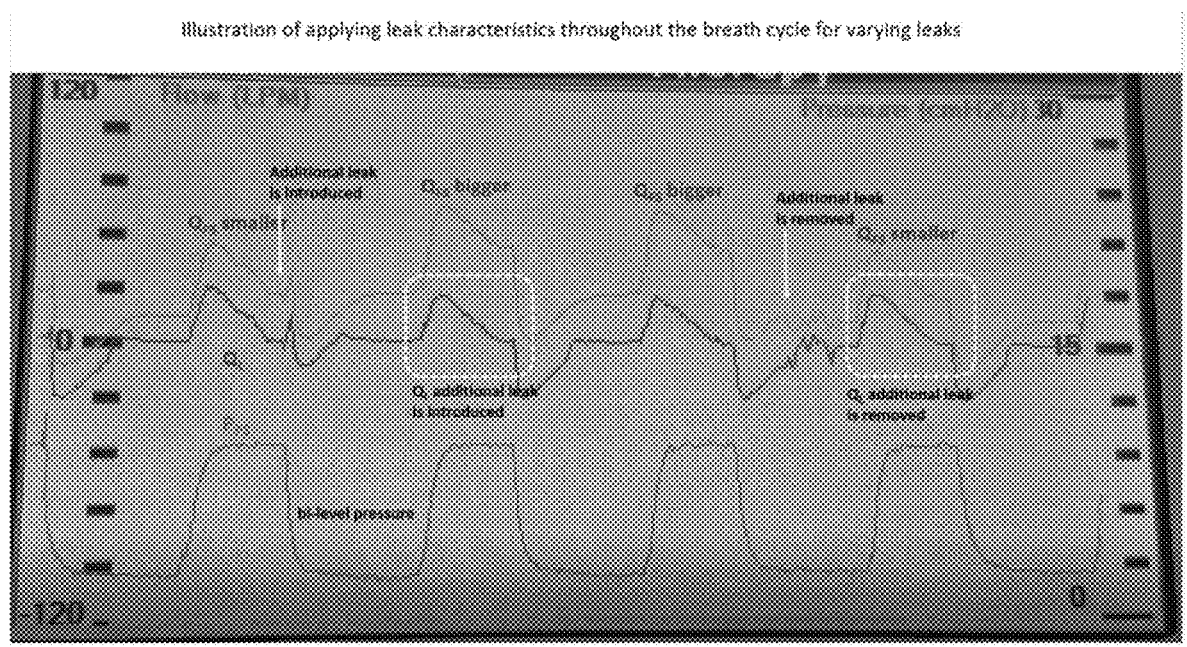
FIG. 9 is a graphical depiction of applied leak characteristics throughout the breath cycle for varying leaks according to one example.

Embodiments of the invention have been applied throughout the breath cycle, for example during inspiration and exhalation in order to accurately determine the net flow to the patient (lung). With reference now to FIG. 9, leak characteristics are applied throughout the breath cycle for varying leaks. $Q_L = Q_{FS} - Q_{TL}$, i.e., net patient flow (lung flow) equals to the total flow from the flow generator minus total leak (both intentional and unintentional leaks). The red waveform ($Q_L$) is consistent for varying amount of unintentional leaks. In this particular example, 100% of additional (unintentional) leak was introduced—see second waveform. $Q_{FS}$ (green waveform) includes both intentional ($Q_{IL}$) and unintentional ($Q_{UL}$) leaks. $Q_{FS}$ smaller is with intentional leak only. $Q_{FS}$ bigger includes both intentional and unintentional leaks.

Figure 10:
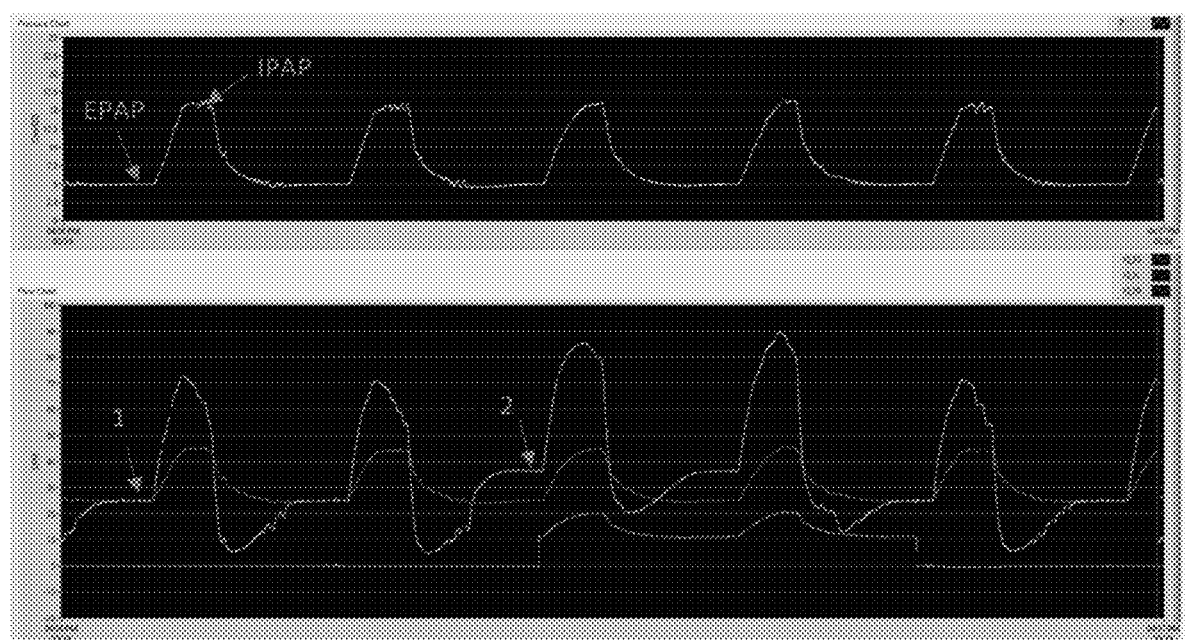
FIG. 10 is a graphical depiction of leak compensation using the relationship between intentional and unintentional leak according to one example.

With reference now to the example in FIG. 10, pressure and flow charts during a normal ventilating operation are shown. Pressure is set at EPAP=5 cmH$_2$O and IPAP=15 cmH$_2$O. The air flow chart has three components: $Q_{FS}$, flow sensor measurement shown in white, $Q_{IL}$ intentional leak shown in red, and $Q_{UL}$, unintentional leak shown in green. The algorithm works as follows: A user selects the patient interface type to provide $Q_{IL}(p)$ data to the algorithm.

Using this general equation relating the different air flows, $$Q_{FS}(t) = Q_{IL}(P,t) + Q_{UL}(t) + Q_L(t)$$

The system looks for the following condition, $$Q_L = 0; \quad Q_{FS} = Q_{IL} + Q_{UL}$$

Which happens at point 1 and 2 when, $$P_{PS} \cong \text{EPAP} = 5 \text{ cmH}_2\text{O}$$

$$Q_{FS}(1) = 25 \text{ LPM}; \quad Q_{FS}(2) = 36 \text{ LPM}$$

$$Q_{IL}(1) = 25 \text{ LPM}; \quad Q_{IL}(2) = 25 \text{ LPM}$$

Solving for $Q_{UL}$ at point 1 and 2:

$$Q_{UL}(1) = Q_{FS}(1) - Q_{IL}(1) = 25 - 25 = 0 \text{ LPM}$$

$$Q_{UL}(2) = Q_{FS}(2) - Q_{IL}(2) = 36 - 25 = 11 \text{ LPM}$$

Point 1 shows that there is no unintentional leak. Point 2 shows that unintentional leak is introduced. α, ratio between $Q_{UL}$ to $Q_{IL}$, can be calculated here $$\alpha = Q_{UL}/Q_{IL} = 11/25$$

The ratio, α is then applied at other pressure points to determine the unintentional leak until a new ratio is found.

$$Q_{UL}(t) = 11/25 Q_{IL}(P,t)$$

Figure 11:
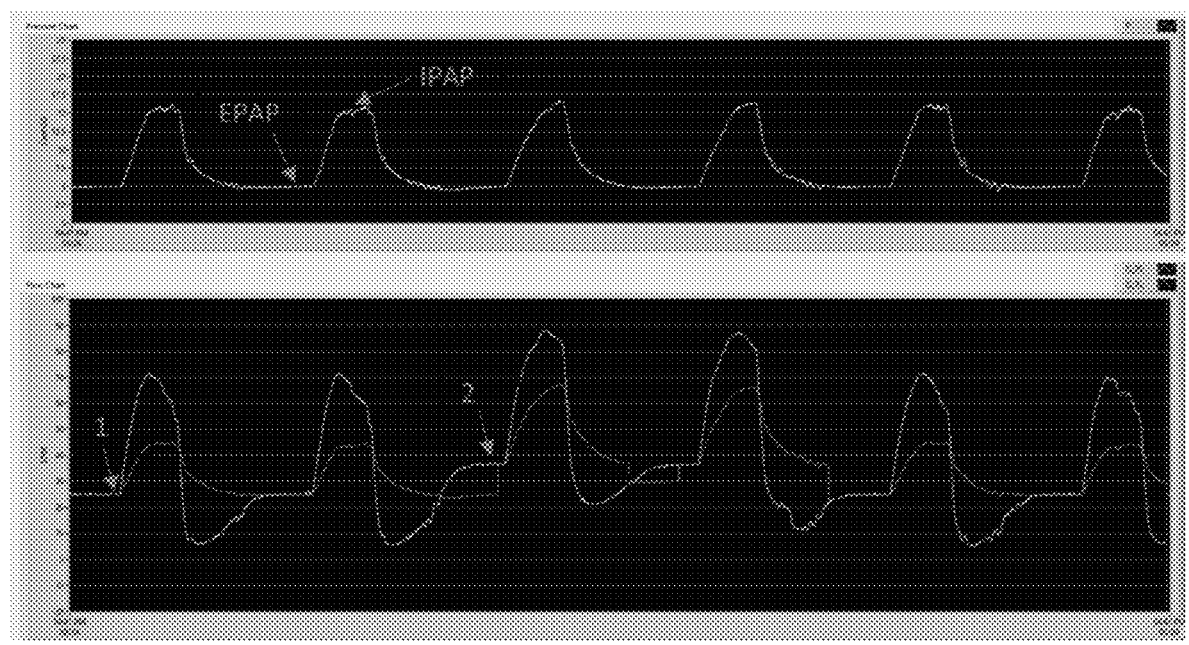
FIG. 11 is a graphical depiction of pressure and flow charts during a normal ventilating operation according to one example.

With reference now to the example in FIG. 11, pressure and flow charts during a normal ventilating operation are shown. Pressure is set at EPAP=5 cmH$_2$O and IPAP=15 cmH$_2$O. The air flow chart has three components: $Q_{FS}$, flow sensor measurement shown in white and $Q_{TL}$, total leak shown in red. The algorithm works as follows: Using this general equation relating the different air flows.

$$Q_{FS}(t) = Q_{TL}(t) + Q_L(t)$$

The system finds the points which satisfy the following condition, $$Q_L = 0; \quad Q_{FS} = Q_{TL}$$

Which happens at point 1 and 2 when, $$P_{PS} \cong \text{EPAP} = 5 \text{ cmH}_2\text{O}$$

$$Q_{FS}(1) = Q_{TL}(1) = 25 \text{ LPM}$$

$$Q_{FS}(2) = Q_{TL}(2) = 36 \text{ LPM}$$

The system plug the corresponding flow and pressure values at point 1 and 2 into an equation or combination of equations modeling flow orifice. Darcy Weisbach's equation is used here to demonstrate.

$$P_{PS} = \frac{8f\rho Q_{TL}^2 L}{D^5 \pi^2}$$

Where the following are known,
L=length of flow path
f=flow coefficent
ρ=air density
D, orifice diameter can be calculated at the point 1 and 2 to be,
D (1)=5.9 mm
D (2)=6.8 mm The orifice diameter at point 2 is larger because additional leak is introduced. The orifice diameter values are then applied at other pressure points to find the total leak. Again, Darcy Weisbach's equation is used here for the sake of providing an example. The system may use different function or multiple functions.

$$Q_{TL}(P, t) = \sqrt{\frac{P_{Ps} D^5 \pi^2}{8 f \rho L}}$$

Where
$Q_{FS}$ Flow @Flow Sensor
$Q_{IL}$ Intentional Leak
$Q_{UL}$ Unintentional Leak
$Q_L$ Lung
$Q_{TL}$ Total Leak=$Q_{IL}$+$Q_{UL}$
Q stands for flowrate
$P_{abs}$ absolute pressure
EPAP Expiratory Positive Airway Pressure
ρ (density of gas) constant 1.22
F constant 0.045 (empirically derived)
α coefficient
D diameter of orifice
L length of patient tube, e.g., 6 ft The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A flow generation system comprising:
   an airflow generator connected in-line to a flow sensor, a pressure sensor and a patient interface connection by a first gas flow circuit; and
   a controller electrically coupled to the airflow generator, the flow sensor and the pressure sensor;
   wherein the airflow generator is configured to change speed based on a control signal received from the controller, the control signal based on a first flow value measured from the flow sensor and an unintentional leak flow value that is derived from a proportional relationship with a predetermined intentional leak flow value.

2. The flow generation system of claim 1, wherein the intentional leak flow value is determined at least partially by a selected patient interface orifice size.

3. The flow generation system of claim 1, wherein the control signal is at least partially driven by a flowrate value of the lungs $Q_L(t)$ that is determined by satisfying the equations:

$$Q_{FS}(t) = Q_{IL}(p,t) + Q_{UL}(p,t) + Q_L(t)$$

when $P_{PS}(t) \cong$ EPAP, $$Q_{FS}(t) = Q_{IL}(t) + Q_{UL}(t)$$

$$Q_{UL}(p,t) = \alpha \cdot Q_{IL}(p,t), \text{ and}$$

where $P_{PS}$ as used herein means pressure as measured by the Pressure Sensor,
$Q_{FS}$ as used herein means flowrate as measured by the Flow Sensor,
$Q_{IL}$ as used herein means flowrate at the Intentional Leak site,
$Q_{UL}$ as used herein means flowrate at the Unintentional Leak site,
$Q_L$ as used herein means flowrate at the Lungs, and
EPAP as used herein means Expiratory Positive Airway Pressure.

4. The flow generation system of claim 3, wherein $P_{PS}(t) \cong$ EPAP when $P_{PS}(t)$ is within 0.5 cmH$_2$O from EPAP.

5. The flow generation system of claim 3, wherein $P_{PS}(t) \cong$ EPAP when $P_{PS}(t)$ is within 0.2 cmH$_2$O from EPAP.

6. The flow generation system of claim 3, wherein $P_{PS}(t) \cong$ EPAP when $P_{PS}(t)$ is within 0.1 cmH$_2$O from EPAP.

7. The flow generation system of claim 3, wherein $P_{PS}(t) \cong$ EPAP when $P_{PS}(t)$ is within 1 cmH$_2$O from EPAP.

8. The flow generation system of claim 1, wherein the control signal is at least partially driven by a flowrate of the lungs $Q_L(t)$ that is determined by satisfying the equations:

$$Q_{FS}(t) = Q_{IL}(p,t) + Q_{UL}(p,t) + Q_L(t)$$

when $P_{PS}(t) \cong$ EPAP, $$Q_{FS}(t) = Q_{IL}(t) + Q_{UL}(t)), \text{ and}$$

where $P_{PS}$ as used herein means pressure as measured by the Pressure Sensor,
$Q_{FS}$ as used herein means flowrate as measured by the Flow Sensor,
$Q_{IL}$ as used herein means flowrate at the Intentional Leak site,
$Q_{UL}$ as used herein means flowrate at the Unintentional Leak site,
$Q_L$ as used herein means flowrate at the Lungs, and
EPAP as used herein means Expiratory Positive Airway Pressure.

9. The flow generation system of claim 8 wherein $P_{PS}(t) \cong$ EPAP when $P_{PS}(t)$ is within 0.5 cmH$_2$O from EPAP.

10. The flow generation system of claim 8 wherein $P_{PS}(t) \cong$ EPAP when $P_{PS}(t)$ is within 0.2 cmH$_2$O from EPAP.

11. The flow generation system of claim 8, wherein $P_{PS}(t) \cong$ EPAP when $P_{PS}(t)$ is within 0.1 cmH$_2$O from EPAP.

12. The flow generation system of claim 8, wherein $P_{PS}(t) \cong$ EPAP when $P_{PS}(t)$ is within 1 cmH$_2$O from EPAP.

13. The flow generation system of claim 1, wherein an orifice equation for a total leaks value that is used to at least partially drive the control signal is modeled using an empirical equation.

14. The flow generation system of claim 1 further comprising:
   a humidifier connected to the first gas flow circuit upstream of the patient interface connection and downstream of both the flow sensor and pressure sensor.

15. The flow generation system of claim 1, wherein the airflow generator is an air pump.

16. The flow generation system of claim 1, wherein the flow generation system is a ventilator.

17. The flow generation system of claim 1 further comprising:
- a bacteria filter in-line with a second gas flow circuit, wherein the second gas flow circuit is connected to a first junction upstream of the patent interface connection and a second junction downstream of the flow sensor and pressure sensor.

18. The flow generation system of claim 17, wherein the second gas flow circuit includes a check valve upstream of the bacteria filter.

19. The flow generation system of claim 17, wherein the bacteria filter is part of a removable cartridge that comprises a portion of the first and second gas flow circuits.

20. The flow generation system of claim 1 further comprising:
- a heat moisture exchanger and bacteria filter in-line with the first gas flow circuit upstream of the patient interface connection and downstream of the flow sensor and pressure sensor.

* * * * *